United States Patent
Partanen et al.

(10) Patent No.: US 10,099,069 B2
(45) Date of Patent: Oct. 16, 2018

(54) THERAPEUTIC APPARATUS AND METHOD FOR HEATING A SUBJECT

(75) Inventors: Ari Ilkka Mikael Partanen, Bethesda, MD (US); Matthew Robert Dreher, Rockville, MD (US); Pavel Sergeyevich Yarmolenko, Silver Spring, MD (US); Antti Johannes Viitala, Espoo (FI); Julia Kristina Enholm, Helsingfors (FI); Max Oskar Kohler, Espoo (FI)

(73) Assignees: Profound Medical Inc., Mississauga, CA (US); National Institutes of Health, Bethesda, MD (US)

( * ) Notice: Subject to any disclaimer, the term of this patent is extended or adjusted under 35 U.S.C. 154(b) by 391 days.

(21) Appl. No.: 13/879,412

(22) PCT Filed: Oct. 11, 2011

(86) PCT No.: PCT/IB2011/054485
§ 371 (c)(1),
(2), (4) Date: Apr. 15, 2013

(87) PCT Pub. No.: WO2012/049628
PCT Pub. Date: Apr. 19, 2012

(65) Prior Publication Data
US 2013/0217950 A1 Aug. 22, 2013

Related U.S. Application Data

(60) Provisional application No. 61/393,469, filed on Oct. 15, 2010.

(30) Foreign Application Priority Data

Feb. 15, 2011 (EP) ..................................... 11154471

(51) Int. Cl.
A61N 7/00 (2006.01)
A61N 7/02 (2006.01)
(Continued)

(52) U.S. Cl.
CPC ................. *A61N 7/00* (2013.01); *A61N 7/02* (2013.01); *G01R 33/4814* (2013.01);
(Continued)

(58) Field of Classification Search
CPC ........... A61B 2017/00084; A61B 2018/00642; A61B 2018/00666; A61B 2018/00678;
(Continued)

(56) References Cited

U.S. PATENT DOCUMENTS 6,542,767 B1 4/2003 McNichols et al.
2007/0239062 A1 10/2007 Chopra et al.
(Continued)

FOREIGN PATENT DOCUMENTS

DE 102007060189 A1 2/2009
EP 2223719 A1 9/2010
(Continued)

OTHER PUBLICATIONS

Kohler, M. O., et al.; Volumetric HIFU ablation under 3D guidance of rapid MRI thermometry; 2009; Med. Phys.; 36 (8)3521-3535.
(Continued)

*Primary Examiner* — Ruth S Smith
(74) *Attorney, Agent, or Firm* — Intrinsic Law Corp.

(57) ABSTRACT

A therapeutic apparatus (900, 1000) comprising a high intensity focused ultrasound system (904) for heating a target zone (940, 1022). The therapeutic apparatus further comprises a magnetic resonance imaging system (902). The therapeutic apparatus further comprises a memory (952) containing machine executable instructions (980, 982, 984, 986, 988, 990) for execution by a processor (944). Execution
(Continued)

of the instructions cause the processor to: generate (702, 802) heating commands (964) which cause the high intensity focused ultrasound system to sonicate the subject; repeatedly acquire (704, 804) magnetic resonance data (954) during execution of the heating commands; repeatedly calculate (706, 806) a spatially dependent parameter (970); and repeatedly modify (708, 808) the heating commands in accordance with the spatially dependent parameter such that within the target zone the spatially dependent parameter remains below a first predetermined threshold and above a second predetermined threshold.

18 Claims, 11 Drawing Sheets

(51) Int. Cl.
 *A61B 17/00* (2006.01)
 *A61B 18/00* (2006.01)
 *A61N 5/10* (2006.01)
 *G01R 33/48* (2006.01)
 *G01R 33/50* (2006.01)
 *A61B 90/00* (2016.01)

(52) U.S. Cl.
 CPC ............ *A61B 2017/00084* (2013.01); *A61B 2018/00642* (2013.01); *A61B 2018/00666* (2013.01); *A61B 2018/00678* (2013.01); *A61B 2018/00791* (2013.01); *A61B 2090/374* (2016.02); *A61N 5/10* (2013.01); *A61N 2005/1085* (2013.01); *A61N 2005/1087* (2013.01); *G01R 33/4804* (2013.01); *G01R 33/50* (2013.01)

(58) Field of Classification Search
 CPC .... A61B 2018/00791; A61B 2090/374; A61N 2005/1085; A61N 2005/1087; A61N 5/10; A61N 7/00; A61N 7/02; G01R 33/4804; G01R 33/4814; G01R 33/50
 See application file for complete search history.

(56) References Cited

U.S. PATENT DOCUMENTS

| | | |
|---|---|---|
| 2009/0088623 A1 | 4/2009 | Vortman et al. |
| 2010/0280356 A1 | 11/2010 | Kohler et al. |

FOREIGN PATENT DOCUMENTS

| | | |
|---|---|---|
| GB | 2450249 A | 12/2008 |
| WO | 2006136912 A1 | 12/2006 |
| WO | 2007047247 A1 | 4/2007 |
| WO | 2009090579 A1 | 7/2009 |
| WO | 2011017168 A2 | 2/2011 |
| WO | 2011045695 A1 | 4/2011 |

OTHER PUBLICATIONS

Ehnholm, J. K., et al.; Improved Volumetric MR-HIFU Ablation by Robust Binary Feedback Control; 2010; IEEE Trans. on Biomedical Engineering; 57(1)103-113.

Planning images:

Temperature mapping:

THERAPEUTIC APPARATUS AND METHOD FOR HEATING A SUBJECT

CROSS REFERENCE TO RELATED APPLICATIONS

This application is a national filing of PCT application Serial No. PCT/IB2011/054485, filed Oct. 11, 2011, published as WO 2012/049628 A1 on Apr. 19, 2012, which claims the benefit of U.S. provisional application Ser. No. 61/393,469 filed Oct. 15, 2010 and EP application serial no. 11154471.4 filed Feb. 13, 2011, both of which are incorporated herein by reference.

TECHNICAL FIELD

The invention relates to magnetic resonance guided high intensity focused ultrasound therapy, in particular to the controlled heating of a target zone in a subject.

BACKGROUND OF THE INVENTION

The invention pertains to a therapy system comprising:
a therapy module to direct a therapeutic action to a target along successive trajectories in a target region that includes the target
a thermometry module to measure temperature a measurement field and in particular to compute a thermal dose,
a control module to control the therapy module to apply the therapeutic action along the respective trajectories on the basis of the measured temperature and/or thermal dose,
wherein the successive trajectories are located in the target zone.

Such a therapy system is known from the international application WO2009/090579-A1 (PH009795).

Mild hyperthermia (HT) is a therapeutic technique in which tissue is heated to temperatures (e.g., 38-45° C.) above body temperature, but below ablative temperatures. These hyperthermia treatments may result in physiological (e.g., perfusion) and cellular (e.g., gene expression) changes that improve the therapeutic effectiveness when used in conjunction with chemotherapy or radiation therapy. HT induces a multitude of changes, which provide clinical benefits that make it synergistic with many chemotherapeutic agents and radiation therapy. In addition to physiological and cellular changes, hyperthermia may be used with temperature responsive or non-responsive drug delivery systems to reduce toxicity and improve overall efficacy. One solution for reducing toxicity involves targeting the tumor with temperature sensitive liposomal drug delivery. In experimental work, liposomes have exhibited near complete drug release within 10-20 seconds at mild hyperthermic temperatures (40-42° C.).

There are a number of currently available devices that can heat target tissue to the hyperthermic range. One example is radiofrequency (RF) applicators, which use tuned antennas to transmit RF energy into the body. However, RF applicators are best used to heat deep-seated tumors, due the long wavelengths of RF. Microwave applicators are also used, but are typically used only for superficial tumors due to their small wavelength. Both types can be used in different configurations, with the most common being phased arrays, waveguides, and spiral antennas. A novel, efficient way of performing local hyperthermia is by magnetic resonance guided high intensity focused ultrasound (MR-HIFU), in which focused ultrasound is used for achieving hyperthermia and MR is utilized to monitor the treatment.

MRI provides in vivo temperature maps during HIFU sonication. Feedback can then be realized by real-time evaluation of temperature elevations detected in the tissue, and adapting the power, duration or trajectory of the sonication based on this knowledge. Volumetric feedback has been previously used to thermally ablate tissue, i.e. achieve complete thermal necrosis in the target region (M. Kohler et al., Med. Phys. 36 (8), 3521, August 2009; J. Enholm et al., IEEE Trans. Biomed. Eng., 57 (1), January 2010). The international application WO 2009/090579-A1 mentions binary feedback for MR-HIFU ablation.

SUMMARY OF THE INVENTION

The invention provides for a therapeutic apparatus, a computer program product, a method, and a therapy system.

An insight of the present invention is that for so-called mild-hyperthermia applications it is required to maintain the elevated temperature, e.g. in the range of 40-45°, for a prolonged duration.

Since the optimum temperature for most mild hyperthermia applications is in the 40-45° range (T<40 C causes limited effect, T>45 C may shut down tissue perfusion), a completely different approach for mild hyperthermia is required. Mild hyperthermia feedback differs from ablative feedback in that the temperature is raised to a level capable of inducing necrosis (usually >55 C) and then letting the tissue cool down, instead mild hyperthermia feedback maintains the temperature in the target region at a desired level for a prolonged duration. During this time, e.g. the power and trajectory can be adjusted for optimum results. Furthermore, the mild hyperthermia implementation results in a flat or homogeneous temperature profile across the heated region in comparison to the sharp spatial gradients found in the ablative algorithm. The binary feedback algorithm known from WO 2009/090579-A1 was incapable of maintaining mild hyperthermia for a prolonged duration, but instead stopped the sonication after the final subtrajectory had reached its end criteria (usually a mean temperature in the range of 55-58° C.).

In the mild hyperthermia feedback implementation of the invention, there are anywhere from 1 to N (1–N) heating subtrajectories, 1 to N (1–N) (temperature maintaining subtrajectories, and one wait subtrajectory. Trajectory geometry and size, and sonication power of the heating and maintaining subtrajectories are set by the user from the user interface, and can be adjusted during a sonication. Typically the subtrajectories are concentric, e.g. concentric circles, but their shape can be arbitrary. No sonication is performed during the wait subtrajectory. In the initial heat-up phase, sonication is switched from a heating subtrajectory towards the next in a known manner until all subtrajectories are sonicated once. After the sonication of the last heating subtrajectory is complete, sonication is switched to the wait subtrajectory. From the wait subtrajectory, sonication can be switched to any of the maintaining subtrajectories, according to realized action criteria. For each image acquired with the MRI, the criteria of the maintaining subtrajectories are inspected, and if any of the prescribed action criteria have been realized, sonication is switched to that subtrajectory. If conditions for several heat maintaining subtrajectories are fulfilled at the same time, then the one that has prescribed priority is chosen to be sonicated first. From any of the heat maintaining subtrajectories, sonication moves back to the wait subtrajectory once the action criteria of the maintaining subtrajectory have been realized. The resulting advantages of this approach yield a homogeneous and accurate heated region, which is essential for clinical implementation. The binary feedback algorithm provides a simple, non-parametric, and robust feedback control as compared to most available parametric feedback algorithms that can be overly complicated.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Medical image data as used herein encompasses data which is descriptive of anatomical structures of a subject. A magnetic resonance image is a type of medical image data.

MR thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a therapeutic apparatus comprising a high-intensity focused ultrasound system for heating a target zone of a subject. The therapeutic apparatus further comprises a magnetic resonance imaging system for acquiring magnetic resonance data. The therapeutic apparatus further comprises a processor for controlling the therapeutic apparatus. By a processor it is understood that a processor may refer to multiple processors or even multiple computer systems or controllers connected or working cooperatively. The therapeutic apparatus further comprises a memory containing machine executable instructions for execution by the processor. Likewise it is understood that references to a memory may refer to multiple memory locations within a single controller or computer system or even distributed amongst a variety of controllers or computer systems.

Execution of the instructions cause the processor to generate heating commands which cause the high-intensity focused ultrasound system to sonicate the subject in accordance with heating trajectories. 'Heating commands' as used herein are instructions for controlling the high-intensity focused ultrasound system. The heating commands may contain control and command sequences for the high-intensity focused ultrasound system. A 'heating trajectory' as used herein is a collection of individual sonication points. In other words a heating trajectory is a collection of locations which are sequentially heated by the high-intensity focused ultrasound system. The heating commands are generated such that the high-intensity focused ultrasound system sonicates in conjunction with heating trajectories. This is to say more than one trajectory or a collection of sequentially sonicated points are followed when the heating commands are executed by the high-intensity focused ultrasound system.

The processor then sends or transmits the heating commands to the high-intensity focused ultrasound system. This then causes the high-intensity focused ultrasound system to perform sonication along the specified heating trajectories. Next execution of the instructions further cause the processor to repeatedly acquire the magnetic resonance data during execution of the heating commands. The processor generates commands which cause the magnetic resonance imaging system to acquire the magnetic resonance data. Execution of the instructions further causes the processor to repeatedly calculate a spatially dependent parameter from the magnetic resonance data. The spatially dependent parameter may be a physical property of the subject since it may be a local temperature or some other local parameter which is affected by the heating of the various sonication points within the target zone. Execution of the instructions further cause the processor to repeatedly modify the heating commands in accordance with the spatially dependent parameter such that within the target zone the spatially dependent parameter remains below a predetermined threshold and above a second predetermined threshold.

The processor also sends the repeatedly modified heating commands to the high-intensity focused ultrasound system. Essentially the acquisition of magnetic resonance data, the calculation of the spatially dependent parameter and the modification of the heating commands in accordance with the dependent parameter forms a closed feedback system. This allows the spatially dependent parameter to remain below a first predetermined threshold and above a second predetermined threshold. Giving one example, the spatially dependent parameter may be the spatially dependent temperature within the subject. In this way the spatially dependent temperature within the target zone may be below a first predetermined temperature threshold and above a second predetermined temperature threshold.

This embodiment is advantageous because it allows for a system which is able to control a spatially dependent parameter such as the temperature accurately. For instance the temperature may be maintained below a temperature necessary to cause ablation of the tissue. The target zone may then be brought to a controlled temperature for a controlled period of time. This may be used to sensitize the region to make it more sensitive to radiation therapy, it may enable the release of drugs or contrast agents from temperature-sensitive capsules or containers. It should be noted that the first predetermined threshold and the second predetermined threshold may be calculated on the fly or may be specified on the basis of a treatment plan or therapy plan.

In another embodiment the instructions further cause the processor to generate waiting commands, which cause the high-intensity focused ultrasound system to halt sonication for a predetermined time after executing the heating commands. The waiting commands as used herein are commands which cause the high-intensity focused ultrasound system to wait and to not sonicate any portion of the target zone of the subject. The instructions further cause the processor to generate maintaining commands which cause the high-intensity focused ultrasound system to sonicate the subject in accordance with maintaining trajectories. A maintaining trajectory as used herein has an identical meaning with that of the heating trajectories. The maintaining trajectories are essentially sequentially specified sonication points within the target zone. Heating trajectories are used to initially heat the target zone. The maintaining trajectories are used to maintain the temperature in the target zone after the heating period imposed by the waiting commands. Waiting commands may also be interpreted as so called waiting trajectories. The maintaining trajectories in some embodiments may be identical with the heating trajectories.

In other embodiments the maintaining trajectories are distinct trajectories from those of the heating trajectories. In some embodiments the maintaining trajectories may be a subset of sonication points of individual heating trajectories.

The instructions further cause the processor to repeatedly acquire the magnetic resonance data during execution of the maintaining commands. The instructions further cause the processor to repeatedly calculate the spatially dependent parameter from the magnetic resonance data acquired during execution of the maintaining commands. The magnetic resonance data acquired during the execution of the maintaining commands may be used to replace the magnetic resonance data acquired during the execution of the heating commands. Execution of the instructions further cause the processor to repeatedly modify the maintaining commands in accordance with the spatially dependent parameter such that within the target zone the spatially dependent parameter remains below a first predetermined threshold and above a second predetermined threshold. The waiting commands, the maintaining commands and the repeatedly modified maintaining commands may be sent or transmitted by the processor to the high-intensity focused ultrasound system for controlling it.

In this embodiment the high-intensity focused ultrasound system first initially heats the target zone using the heating trajectories. There is then a waiting period which is then followed by a period where maintaining commands are executed to maintain the temperature of the target zone. In some embodiments the waiting commands may be performed alternately with the maintaining commands. That is to say the waiting commands are executed; the system waits, and then the maintaining commands are executed. Then there is another period where there is no sonication and the waiting commands are executed again. The maintaining commands are then executed again. This technique may be repeated as long as it is desired to maintain the spatially dependent parameter between the first predetermined threshold and the second predetermined threshold.

In another embodiment execution of the instructions further cause the processor to acquire repeatedly the magnetic resonance data during execution of the waiting commands. Execution of the instructions further cause the processor to trigger execution of the maintaining commands if a spatially dependent parameter in the target zone is below the second predetermined threshold. Execution of the instructions may also cause the processor to repeatedly calculate the spatially dependent parameter from the magnetic resonance data acquired during execution of the waiting commands. In this embodiment the magnetic resonance data is continued to be acquired during execution of the waiting commands. If the spatially dependent parameter dips below the second predetermined threshold then the execution of the maintaining commands may be triggered.

The spatially dependent parameter may be a single numerical value or it may also be a mapping. For instance the spatially dependent parameter may be something such as the average temperature of the target zone. If the average temperature then dips below the second predetermined threshold then the execution of the maintaining commands is executed. The spatially dependent parameter may also be something for instance as a map such as a temperature map. The first and second predetermined thresholds may then be a condition which is exhibited by the map which causes the triggering.

In another embodiment execution of the instructions further cause the processor to halt sonication if a predetermined maximum sonication duration is exceeded. This embodiment may for instance be useful to prevent a subject from being sonicated too long. For instance for a particular subject the waiting and/or maintaining trajectories may not be sufficient to maintain the spatially dependent parameter between the first predetermined threshold and the second predetermined threshold.

In another embodiment execution of the instructions further cause the processor to allow the spatially dependent parameter to exceed the first predetermined threshold in the target zone if the sonication duration is less than a predetermined minimum sonication duration. In this embodiment the spatially dependent parameter is allowed to exceed the first predetermined threshold if the sonication time is below a predetermined minimum sonication. It should be noted that for this and the previous embodiment the sonication duration is the duration during which the heating and/or maintaining trajectories are executed. Trajectories are performed by sequentially sonicating various volumes within the target zone of the subject.

In another embodiment the spatially dependent parameter is the proton signal intensity. In another embodiment the spatially dependent parameter is the maximum proton signal intensity.

In another embodiment the spatially dependent parameter is the minimum proton signal intensity.

In another embodiment the spatially dependent parameter is the mean proton signal intensity.

In another embodiment the spatially dependent parameter is the mean proton signal intensity.

In another embodiment the spatially dependent parameter is the T1 signal intensity.

In another embodiment the spatially dependent parameter is the maximum T1 signal intensity.

In another embodiment the spatially dependent parameter is the minimum T1 signal intensity.

In another embodiment the spatially dependent parameter is the mean T1 signal intensity.

In another embodiment the spatially dependent parameter is the median T1 signal intensity.

In another embodiment the spatially dependent parameter is the T2 signal intensity.

In another embodiment the spatially dependent parameter is the maximum T2 signal intensity.

In another embodiment the spatially dependent parameter is the minimum T2 signal intensity.

In another embodiment the spatially dependent parameter is the mean T2 signal intensity.

In another embodiment the spatially dependent parameter is the median T2 signal intensity.

In another embodiment the spatially dependent parameter is the T* signal intensity.

In another embodiment the spatially dependent parameter is the minimum T* signal intensity.

In another embodiment the spatially dependent parameter is the maximum T* signal intensity.

In another embodiment the spatially dependent parameter is the mean T* signal intensity.

In another embodiment the spatially dependent parameter is the temperature.

In another embodiment the spatially dependent parameter is the minimum temperature.

In another embodiment the spatially dependent parameter is the mean temperature.

In another embodiment the spatially dependent parameter is the median temperature.

In another embodiment the spatially dependent parameter is the minimum ultrasonic dose.

In another embodiment the spatially dependent parameter is the maximum ultrasonic dose.

In another embodiment the spatially dependent parameter is the median ultrasonic dose.

In another embodiment the spatially dependent parameter is the maximum temperature deviation.

In another embodiment the spatially dependent parameter is the minimum signal intensity.

In another embodiment the spatially dependent parameter is the maximum signal intensity.

In another embodiment the spatially dependent parameter is the mean signal intensity.

In another embodiment the spatially dependent parameter is the median signal intensity.

In another embodiment the spatially dependent parameter is the minimum thermal dose. The 'thermal dose' as used herein encompasses any quantity which is the time integral of a temperature dependent function. The thermal dose may be for instance the time spent above a temperature threshold.

In another embodiment the spatially dependent parameter is the mean thermal dose.

In another embodiment the spatially dependent parameter is the median thermal dose.

In another embodiment the spatially dependent parameter is the maximum thermal dose.

In another embodiment there is more than one spatially dependent parameter. Since the temperature and a parameter which is dependent on the T2 or T* value may both be used. In this case there may be separate first and second predetermined thresholds for each spatially dependent parameter. As was mentioned earlier the values of the spatially dependent parameter may be defined as a global function of the target zone or may be defined as mappings.

In another embodiment the trajectories define concentric circles. The trajectories refer to the heating trajectories and/or the maintaining trajectories. Each of the concentric circles may be considered to be an individual trajectory. If concentric circles are used typically the inner-most circle will be sonicated first and then the next circle of sonication points will be sonicated. This maintains temperature in the central area surrounded by the concentric circles.

In another embodiment the trajectories define concentric spheres. The trajectories refer to the heating trajectories and/or the maintaining trajectories. Instead of placing sonication points in a two-dimensional plane and concentric circles, concentric spheres can be populated with sonication points that are sequentially sonicated.

In another embodiment the trajectories define closed loops. Again the trajectories refer to waiting trajectories and/or maintaining trajectories. The embodiment of the closed loops is very similar to the embodiment of the concentric circles. Instead of being concentric circles there may be progressively larger closed loops which enclose each other.

In another embodiment the trajectories define closed surfaces. The trajectories again refer to the heating trajectories and/or maintaining trajectories. Instead of using concentric spheres larger and larger closed surfaces which enclose each other may be used for defining the trajectories.

In another embodiment the trajectories refer to a single sonication location. Again the trajectories refer to the heating trajectories and/or the maintaining trajectories. For instance a single sonication location may be considered to be a trajectory. Then a collection of single sonication locations may be considered to be a collection of heating trajectories or maintaining trajectories.

In another embodiment the trajectories define the near patterns. Again the trajectories refer to the heating trajectories and/or the maintaining trajectories. In this embodiment the sequentially sonicated points are arranged in lines and multiple trajectories can therefore form linear patterns.

In another embodiment the instructions further cause the processor to receive medical image data. The instructions further cause the processor to receive a treatment plan. The treatment plan is descriptive of the location of the target zone. The instructions further cause the processor to generate the heating trajectories in accordance with the medical image data and the treatment plan. Another similar embodiment exists where the maintaining trajectories are generated instead of the heating trajectories. There is yet another embodiment where the processor generates both heating trajectories and maintaining trajectories. In this embodiment medical image data is received. The processor may segment the image or the medical image data may be pre-segmented. A treatment plan which is descriptive of the location of the target zone is then used in conjunction with the medical image data to identify the location of the target zone in the medical image data and to generate the heating trajectories.

In another embodiment execution of the instructions further causes the processor to receive magnetic resonance data from the magnetic resonance imaging system. In another embodiment execution of the instructions further causes the processor to reconstruct the medical image data from the magnetic resonance data.

In another embodiment the therapeutic apparatus further comprises a radiation therapy system. Execution of the instructions further causes the processor to irradiate a radiation target in the subject after heating the target zone.

In another embodiment the therapeutic apparatus further comprises a radiation therapy system. Execution of the instructions further causes the processor to irradiate the radiation target during heating of the target zone.

In another embodiment the radiation target comprises at least a portion of the target zone. In some instances the radiation target and the target zone may be identical. In another embodiment the radiation target is smaller than the target zone and the radiation target is completely within the target zone. In yet another embodiment the radiation target is larger than the target zone and encompasses the entire target zone.

In another embodiment the radiation therapy system is a proton therapy system.

In another embodiment the radiation therapy system is an x-ray therapy system.

In another embodiment the radiation therapy system is a charged particle therapy system.

In another embodiment the radiation therapy system is carbon iron therapy system.

In another embodiment the radiation therapy system is a gamma radiation source therapy system. Another name for a gamma radiation source therapy system is a gamma knife. Radio isotopes such as cobalt may be used as a radiation source.

In another embodiment the radiation therapy system is a beta particle therapy system. A beta particle therapy system launches high energy beta particles at the subject.

In another embodiment the radiation therapy system is Linac or a linear accelerator.

In another embodiment execution of the instructions further cause the processor to repeatedly calculate a second spatially dependent parameter from the magnetic resonance data. The second spatially dependent parameter is in some embodiments chosen from the previously named spatially dependent parameters. Execution of the instructions further cause the processor to halt sonication of the target zone by the high-intensity focused ultrasound system if a predetermined change in the second spatially dependent parameter occurs. A predetermined change may for instance be an absolute value of the second spatially dependent parameter or it may be such things as a derivative or integral of the second spatially dependent parameter. For instance the values of T1, T2, or T2-* may be used to monitor the release of a contrast agent or drug by the heating of the target zone. One of these aforementioned parameters may be used to indicate the dosage received by the target zone. It is beneficial to halt when the predetermined parameter occurs because then therapy may be ended when it has become effective.

In another aspect the invention provides for a computer program product comprising machine executable instructions for execution by a processor controlling a therapeutic apparatus. The computer program product may for instance be stored on a computer-readable storage medium. The therapeutic apparatus comprises a high-intensity focused ultrasound system for heating a target zone of a subject. The therapeutic apparatus further comprises a magnetic resonance imaging system for acquiring magnetic resonance data. Execution of the instructions causes the processor to generate heating commands which cause the high-intensity focused ultrasound system to sonicate the subject in accordance with heating trajectories. Execution of the instructions further causes the processor to repeatedly calculate a spatially dependent parameter from the magnetic resonance data. Execution of the instructions further causes the processor to repeatedly modify the heating commands in accordance with the spatially dependent parameter such that within the target zone the spatially dependent parameter remains a first predetermined threshold and above a second predetermined threshold.

In another aspect the invention provides for a method of operating a therapeutic apparatus. The therapeutic apparatus comprises a high-intensity focused ultrasound system for heating a target zone of a subject. The therapeutic apparatus further comprises a magnetic resonance imaging system for acquiring magnetic resonance data. The method comprises the step of generating heating commands which cause the high-intensity focused ultrasound system to sonicate the subject in accordance with the heating trajectories. The method further comprises the step of acquiring repeatedly the magnetic resonance data during execution of the heating commands. The method further comprises the step of calculating repeatedly a spatially dependent parameter from the magnetic resonance data. The method further comprises the step of modifying repeatedly the heating commands in accordance with the spatially dependent parameter such that within the target zone the spatially dependent parameter remains below a first predetermined threshold and above a second predetermined threshold. This method may be implemented by a computer or a processor. This method therefore also provides for a computer implemented method.

In some embodiments the method may further comprise the step of injecting a subject with a heat-sensitive therapeutic agent or a heat-sensitive contrast agent. By heat-sensitive it is meant that the therapeutic drug or agent or contrast agent is released when heated above a certain temperature for a predetermined period of time.

In another aspect the invention provides for a therapy system comprising a therapy module to direct a therapeutic action to a target along successive trajectories in a target region that includes the target. The therapy module may be the high-intensity focused ultrasound system. The therapeutic action may be sonicating the target zone of the subject. The therapy system further comprises a thermometry module to measure temperature, a measurement field and in particular to compute a thermal dose. The thermometry module may be the magnetic resonance imaging system. The magnetic resonance imaging system may acquire magnetic resonance thermometry data and use this to determine locally dependent temperature within the subject.

The system further comprises a control module to control the therapy module to apply the therapeutic action along the respective trajectories on the basis of the measured temperature and/or thermal dose. The control module may be the processor for controlling the therapeutic apparatus. The successive trajectories are located in the target zone and the set of trajectories include a heating subset of heating sub-trajectories during which the temperature in the target region is increased to an elevated temperature level. The set of trajectories further include a maintaining subset of maintaining sub-trajectories during which the temperature in the target region is maintained at the elevated temperature. The sub-trajectories optionally include a waiting period applied between carrying out the heating subset and the maintaining subset. The heating subset of heating sub-trajectories corresponds to the heating trajectories. The maintaining subset of maintaining sub-trajectories corresponds to the maintaining trajectories. The waiting period corresponds to the waiting commands.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
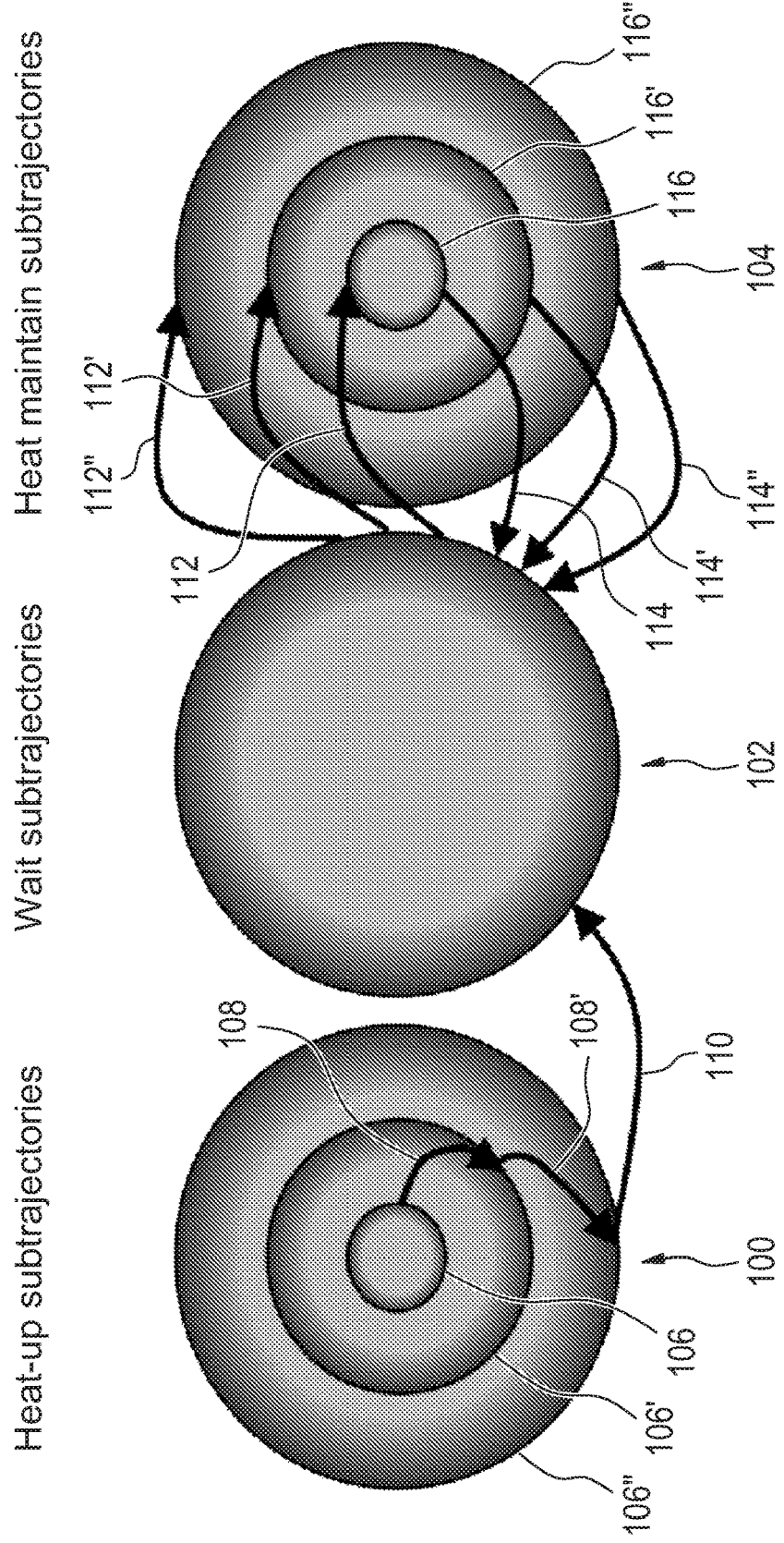
FIG. 1 graphically illustrates an embodiment of the method according to the invention.

One continuous ultrasonic exposure is called a sonication. A path outlined by the ultrasonic focal point throughout one sonication is called a sonication trajectory. The focal-point movement may be achieved by electronic deflection, mechanical movement or a combination of the two. The trajectory may be in one-, two- or in three dimensions. A trajectory can be run multiple times during a sonication. Trajectory can consist of subtrajectories, which can consist of a number of focal points distributed along the subtrajectory path. Focal point distribution need not be even. Subtrajectories can be single points (as few as one pixel or fraction of), or open or closed paths of the focal points, and can take any arbitrary geometry or size independent of each other. All subtrajectories, including their possible repetitions, make up the trajectory in its entirety. Subtrajectories are not fixed, and their geometry and size can be adjusted during a sonication. An example of subtrajectories and a single trajectory can be seen in FIG. 1. Subtrajectories are often, however, concentric circles as shown in FIG. 1, as for example for the Sonalleve® MR-HIFU platform.

Trajectories, subtrajectories and single focal points can be sonicated at a known power, which can be adjusted during a sonication at will.

Trajectories, subtrajectories and single focal points can have any sonication duration, which can be adjusted during a sonication at will.

The sonication time per point and the sonication order of the points is chosen to make the temperature rise along the subtrajectories and trajectory produce a homogeneous spatial temperature distribution.

The action-criteria are the actual logical conditions, which are used to control the progress of the mild hyperthermia feedback algorithm. The criteria are abort/and/or type statements, which when fulfilled return the information on how to proceed with the sonication. There can be multiple kinds of action-criteria, including stop criteria and switch criteria.

The stop criteria monitor the voxels from the entire trajectory and check if the sonication should be stopped or aborted. The stop criteria can therefore both include criteria, which indicate that the sonication has been completed successfully and safety criteria, which indicate problems and abort the sonication prematurely.

The switch criteria are subtrajectory specific, i.e. only monitor the voxels related to the subtrajectory being sonicated. The switch criteria monitor whether one subtrajectory should be switched to the next. The switch criteria can also include subtrajectory specific safety criteria, which abort the sonication if the condition is fulfilled. Possible criteria include but are not limited to: maximum time, minimum time, maximum temperature, minimum temperature, mean temperature, median temperature, minimum dose, maximum dose, median dose, maximum temperature deviation, minimum signal intensity, maximum signal intensity, mean signal intensity, median signal intensity.

The limits for action criteria can be changed both before and during a sonication.

In the example below and shown in FIG. 1, each subtrajectory is circular and has a fixed power, although these attributes can be adjusted during a sonication based on action criteria.

FIG. 1 graphically illustrates an embodiment of the method according to the invention. In FIG. 1 are shown heating trajectory 100, a waiting period 102, and maintaining trajectory 104. In the Fig. the heating trajectory 100 is referred to as a heat-up trajectory, the waiting period 102 is referred to as the wait sub-trajectory. The maintaining trajectory 104 is referred to as the heat maintaining trajectory.

The heating trajectory 100 are comprised of three heat subtrajectories labeled 106. The innermost heat subtrajectory 106 is performed and then the arrow 108 shows a change to heating subtrajectory 106'. Next heat subtrajectory 106' is performed. After heat subtrajectory 106' is performed there is a shift 108' to heat subtrajectory 106". After heat subtrajectory 106" is performed there is a change 110 to the waiting period 102. This may also be referred to as performing the wait sub-trajectory. When the waiting period is over any one of the maintaining subtrajectories 116, 116', 116" are performed. For instance magnetic resonance imaging may be used to take a thermal map and it may be determined which maintaining subtrajectory 116, 116', 116" should be performed. Line 112 indicates a change to maintaining subtrajectory 116. The arrow labeled 112' indicates a change to heating subtrajectory 116'. The arrow labeled 112" indicates a change to maintaining subtrajectory 116". After a particular sub-trajectory is performed the waiting period may then be returned to. Arrow 114 indicates a return from maintaining subtrajectory 116 to the waiting period 102. Arrow 114' indicates a change from maintaining subtrajectory 116' to the waiting period 102. Arrow 114" indicates a return from heating subtrajectory 116" to the waiting period 102. All or a portion of a maintaining subtrajectory 116, 116', 116" may or may not be performed. During performing the method going between waiting and performing a maintaining subtrajectory 116, 116', 116" may be repeated multiple times.

Mild hyperthermia feedback, an example:
1. Sonication starts. Focal point is moved from one heat-up subtrajectory to the next, until outermost subtrajectory is reached and completed.
2. From the outermost heat-up subtrajectory, sonication is moved to the wait-subtrajectory, which has 0 W power, and there is no sonication.
3. Wait subtrajectory has one collection of switch decisions for each heat maintaining subtrajectory Sonication is moved to a heat maintaining subtrajectory, if e.g. temperature in the monitored ROI drops below defined limit If this happens for several subtrajectories at same point in time, the one that has a prescribed priority is chosen
4. From the heat maintaining subtrajectory, sonication is switched back to the wait subtrajectory when e.g. temperature in the monitored ROI reaches defined limit
5. Repeat steps 3 and 4 until a limit determined by a stop-criteria is fulfilled (e.g. maximum time, mean signal intensity, etc.)

Applications for the mild hyperthermia feedback include MR guided pain palliation, MR guided radiation sensitization, MR guided chemotherapeutic delivery (local drug delivery), MR guided drug activation, MR guided gene delivery and gene expression, and inducing physiological and cellular changes (under MR guidance) in order to provide clinical benefits. The Philips Sonalleve® MR-HIFU system can be used for the abovementioned applications.

Figure 2:
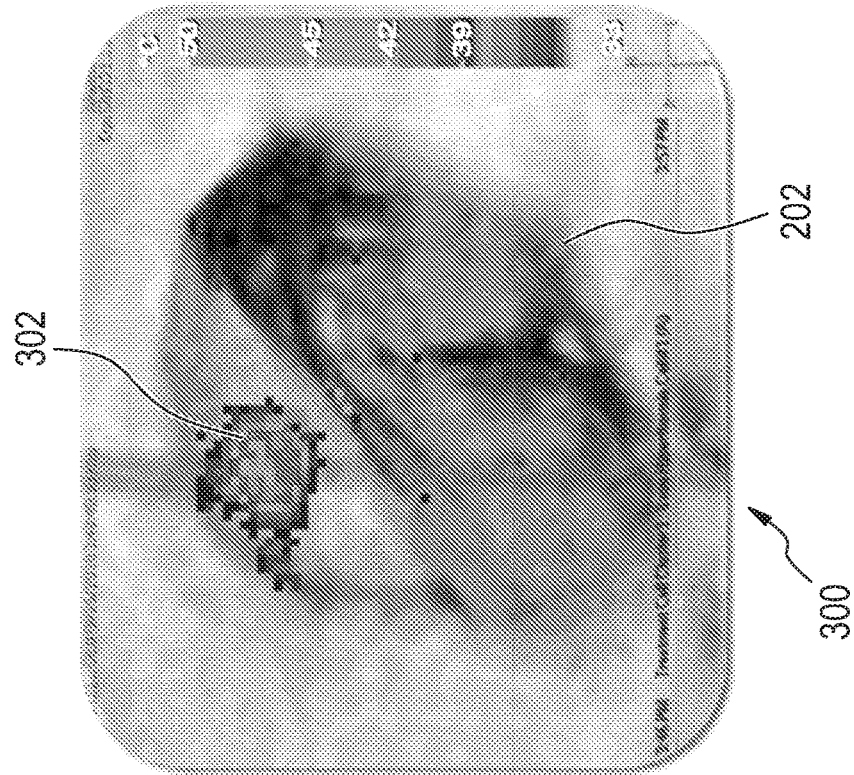
FIG. 2 shows a magnetic resonance image.
Figure 3:
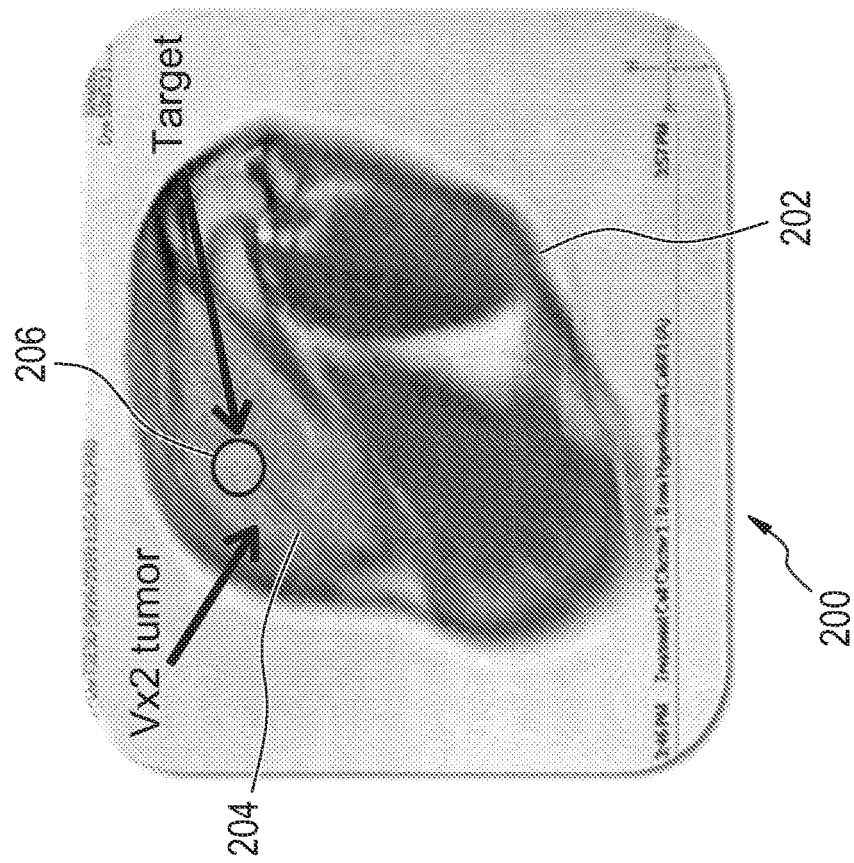
FIG. 3 shows a thermal map.

FIGS. 2 and 3 are used to further demonstrate the effectiveness of the method. FIG. 2 shows a planning image 200. FIG. 3 shows a thermal map 300. Image 200 is an example of a medical image or a magnetic resonance image. Within the planning image a rabbit thigh 202 is visible. Within the rabbit thigh 202 there is a Vx2 tumor 204. Also shown on the map is a target zone 206. The planning image 200 is a magnetic resonance image. During sonication of the target zone 206 and during performing a method according to an embodiment of the invention the target zone 206 was heated. Magnetic resonance thermometry data was acquired during the sonication of the target zone 206 and is shown in a temperature mapping 300. The rabbit thigh 202 is visible in this picture mapping 300. It can be seen that there is a thermally elevated region 302 corresponding to where the target zone 206 is in FIG. 2. The area of the target zone 206 is held between a temperature of 40 and 41 degrees celsius. This is an illustration of the effectiveness of the method.

Figure 4:
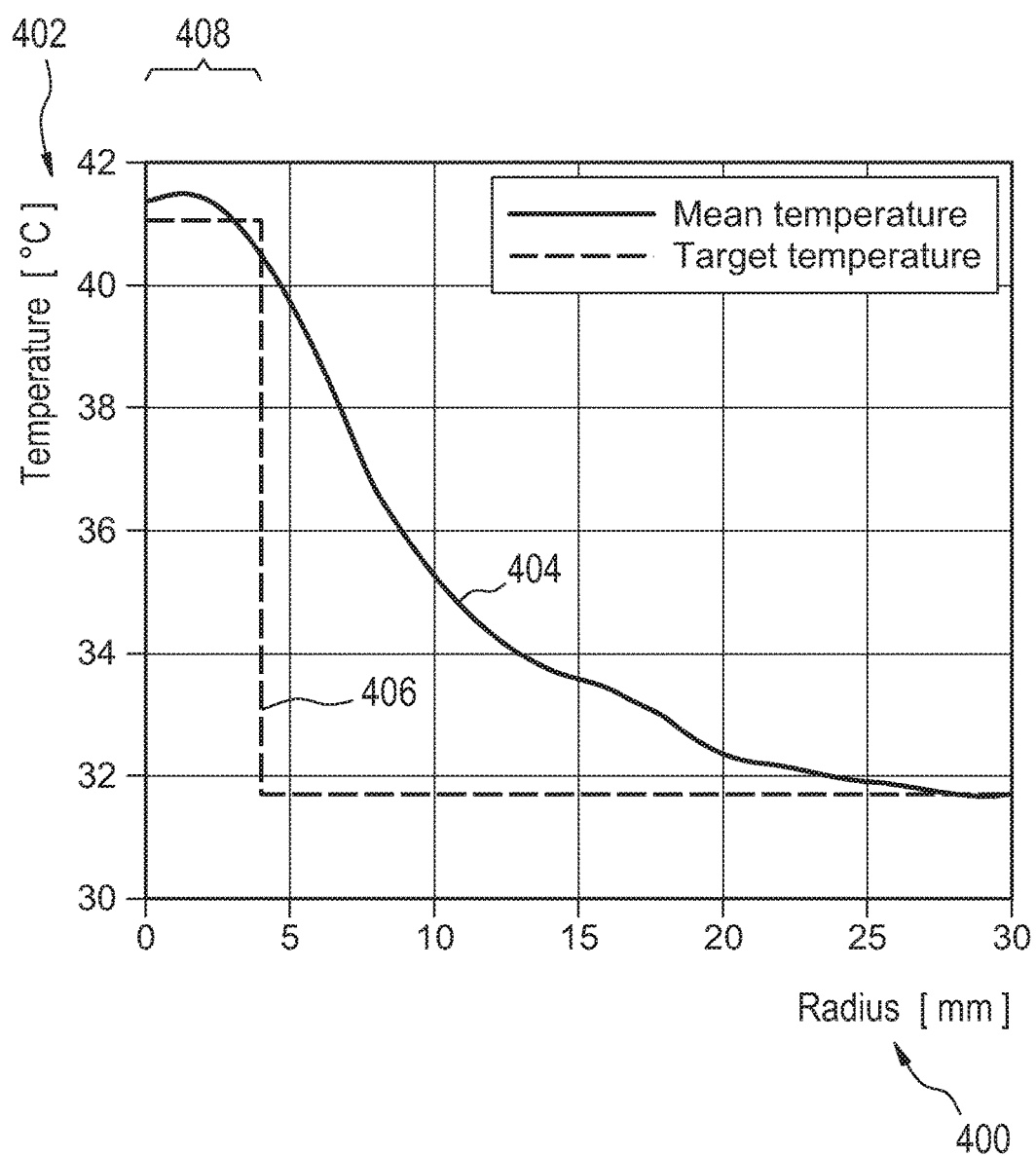
FIG. 4 shows a plot illustrating the effectiveness of the method.

FIG. 4 shows a plot of the radial temperature for the data shown in FIG. 3. The x-coordinate is the radius 400 in millimeters from the center of the target zone 206 shown in FIG. 3, the y-axis labeled 402 is the temperature in degrees Celsius. The line labeled 404 is the mean radial temperature. This is to say for a particular radius around the target zone 206 the mean temperature at that particular radius. The dashed line 406 shows the target temperature. The target temperature of the target zone 206 of FIG. 3 is indicated by the bracket 408. It can be seen that the method keeps the temperature very close to the target temperature. The target temperature in the target zone 408 is set to 41 degrees. The temperature ranges from approximately 40.5 degrees Celsius to 41.5 degrees Celsius.

Figure 5:
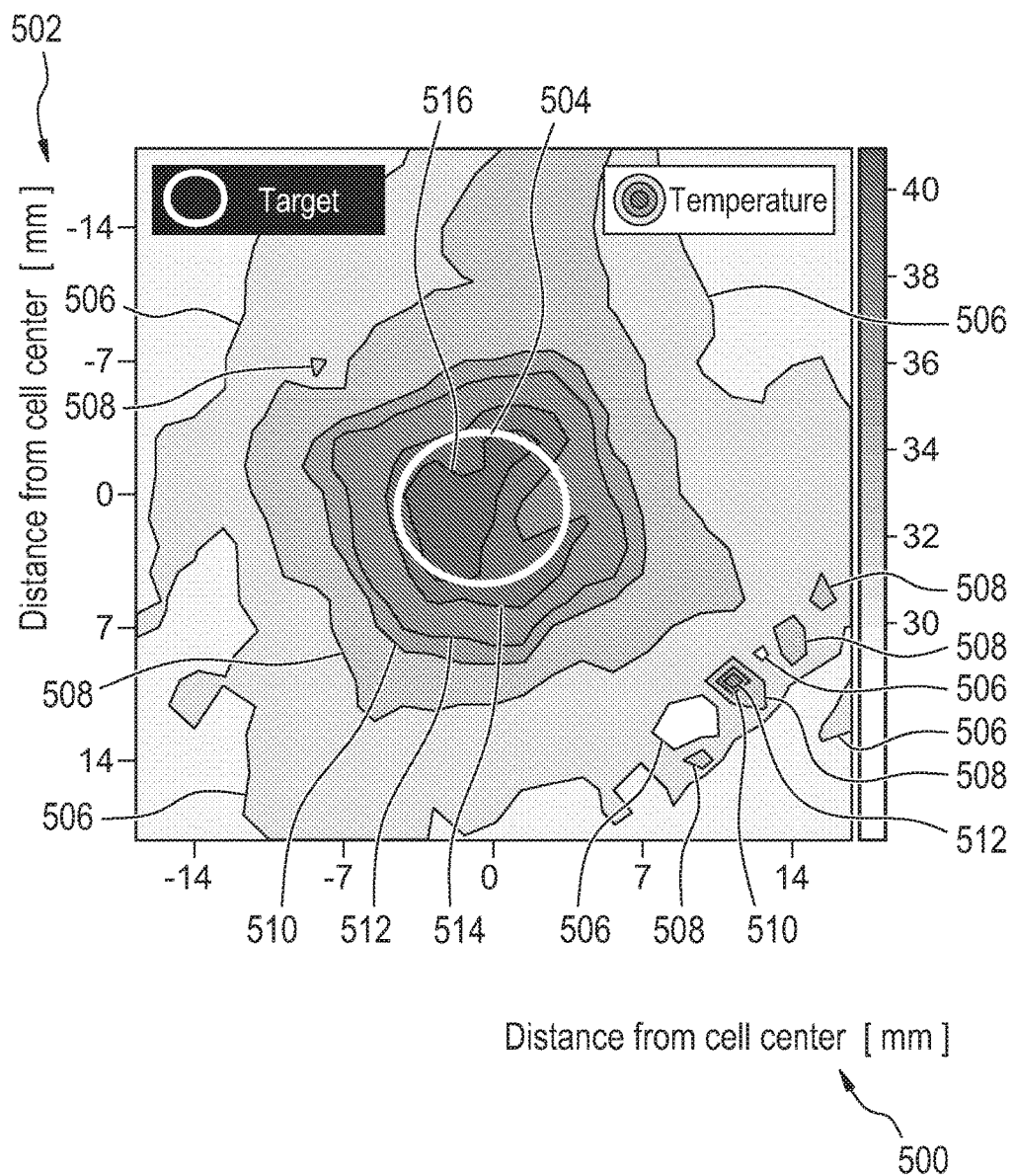
FIG. 5 shows a contour plot illustrating the effectiveness of the method and uniformity of temperature within a targeted area.

FIG. 5 shows a contour plot illustrating the effectiveness of the method. The x-coordinate is the distance from the target zone center and is labeled 500. The y-axis labeled 502 is also the distance from the target zone center. The ring 504 indicates the target zone. Contour lines labeled 506 are 31 degrees Celsius. Contour lines labeled 508 are 35 degrees Celsius. Contour lines labeled 510 are 37 degrees Celsius. Contour lines labeled 512 are 38 degrees Celsius. Contour lines labeled 514 are 40 degrees Celsius. Contour lines labeled 516 are 41 degrees Celsius. The data for the contour plot shown in FIG. 5 was acquired using magnetic resonance thermometry and was also acquired during the treatment of a Vx2 tumor using an embodiment of the method according to the invention which included both heating and maintaining trajectories.

Figure 6:
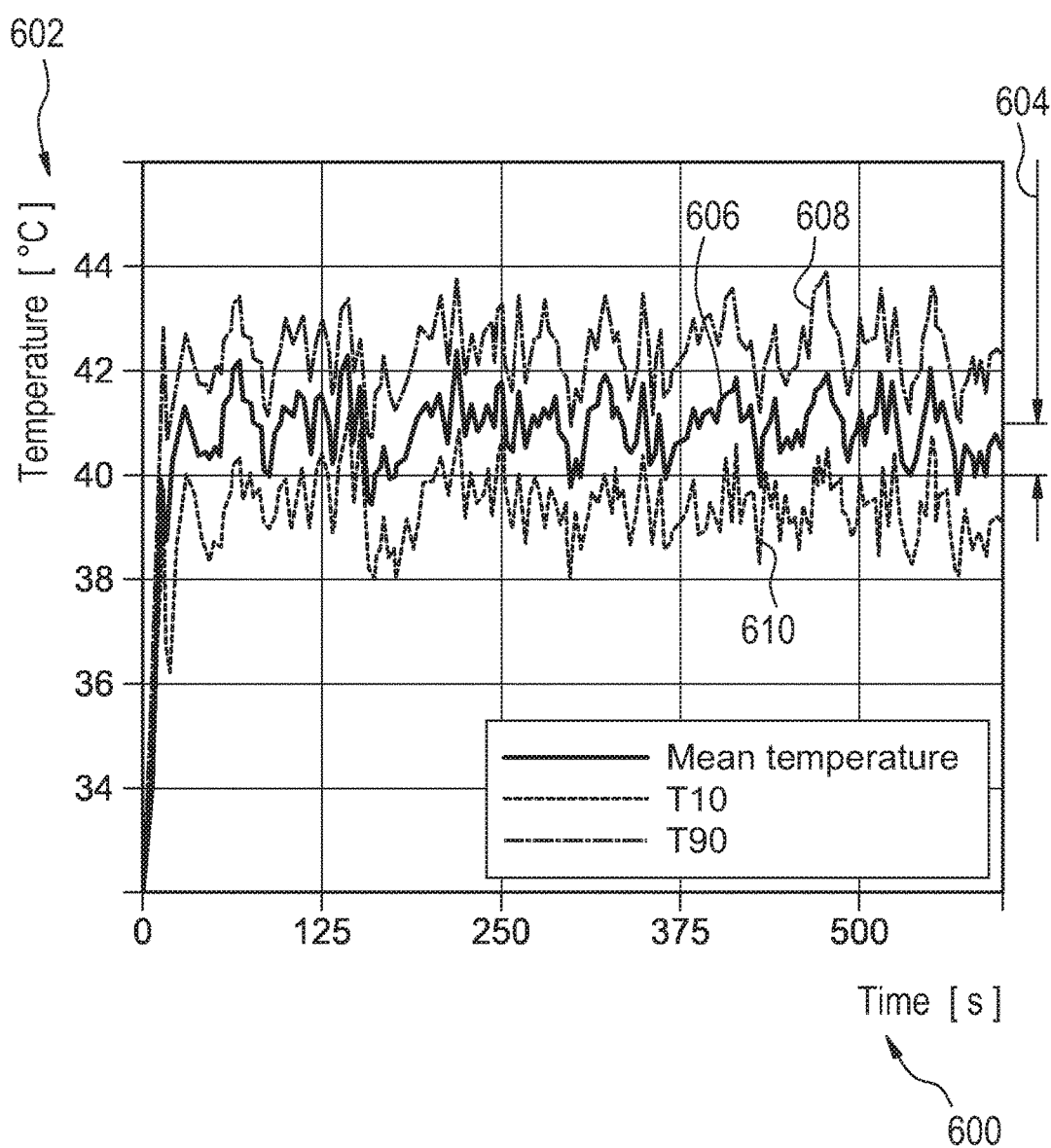
FIG. 6 shows a plot which illustrates the accuracy and stability of heating within a targeted area.

FIG. 6 is a plot which illustrates the accuracy and stability of heating using the method to heat a tumor.

FIG. 6 shows a plot which illustrates the accuracy and stability of heating within a targeted area, in this case again a Vx2 tumor in a rabbit. The x-axis is the time and is labeled 600. The y-axis is labeled 602 and is a temperature in degrees Celsius. The temperature rage indicated by bracket 604 is the target temperature. This is between 40 and 41 degrees Celsius. The curve labeled 606 is the mean temperature in all voxels of the target zone as measured by magnetic resonance thermometry. The dashed line labeled 608 shows the temperature value that 90% of the voxels in the target zone currently below. The dashed line labeled 610 shows the temperature value that 90% of the voxels in the target zone are over. From FIG. 6 it can be seen that the temperature control method is extremely stable and accurate.

Figure 7:
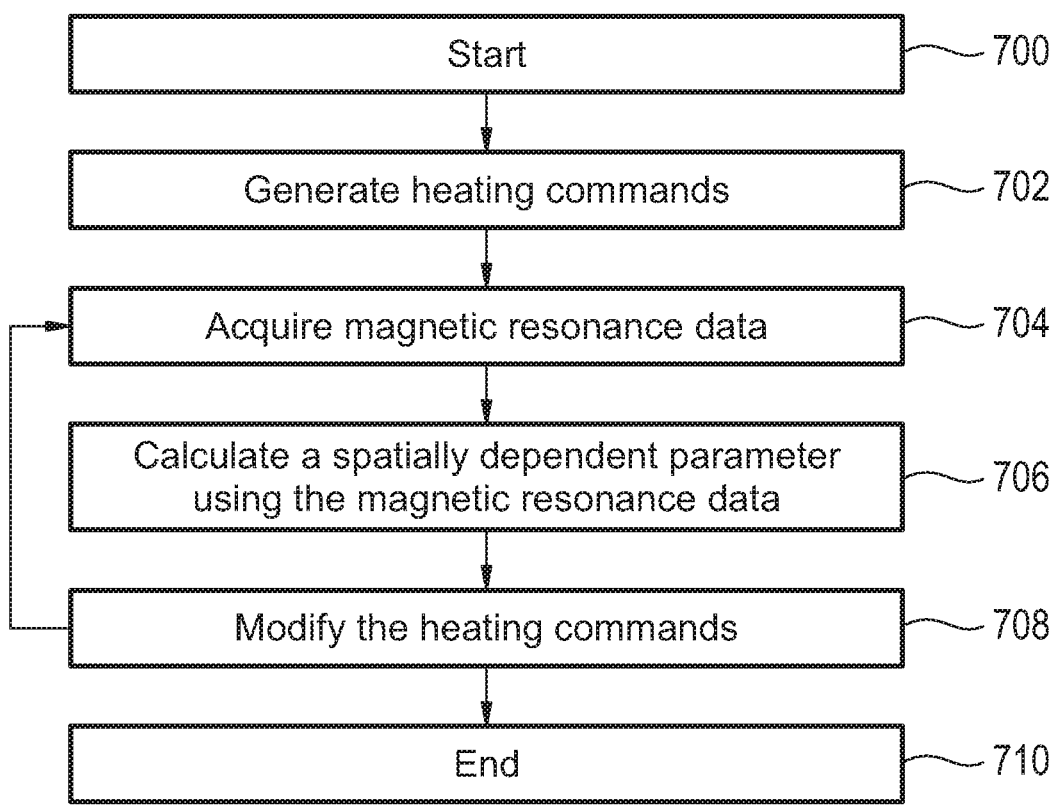
FIG. 7 shows a flow diagram which illustrates a method according to an embodiment of the invention.

FIG. 7 shows a flow diagram which illustrates an embodiment of a method according to the invention. In step 700 the method starts. In step 702 heating commands are generated. In step 704 magnetic resonance data is acquired while the target zone is being heated. The heating normally occurs because the processor has sent the heating commands to the high-intensity focused ultrasound system. In step 706 a spatially dependent parameter is calculated using acquired magnetic resonance data. In step 708 the heating commands are modified and sent to the high-intensity focused ultrasound system. Step 704, 706 and 708 form a closed loop and after the modified heating commands are sent to the high-intensity focused ultrasound system more magnetic resonance data is acquired. This is then again used to calculate a spatially dependent parameter 706 using the magnetic resonance data. This loop 704, 706, 708 is repeated until the method ends 710.

Figure 8:
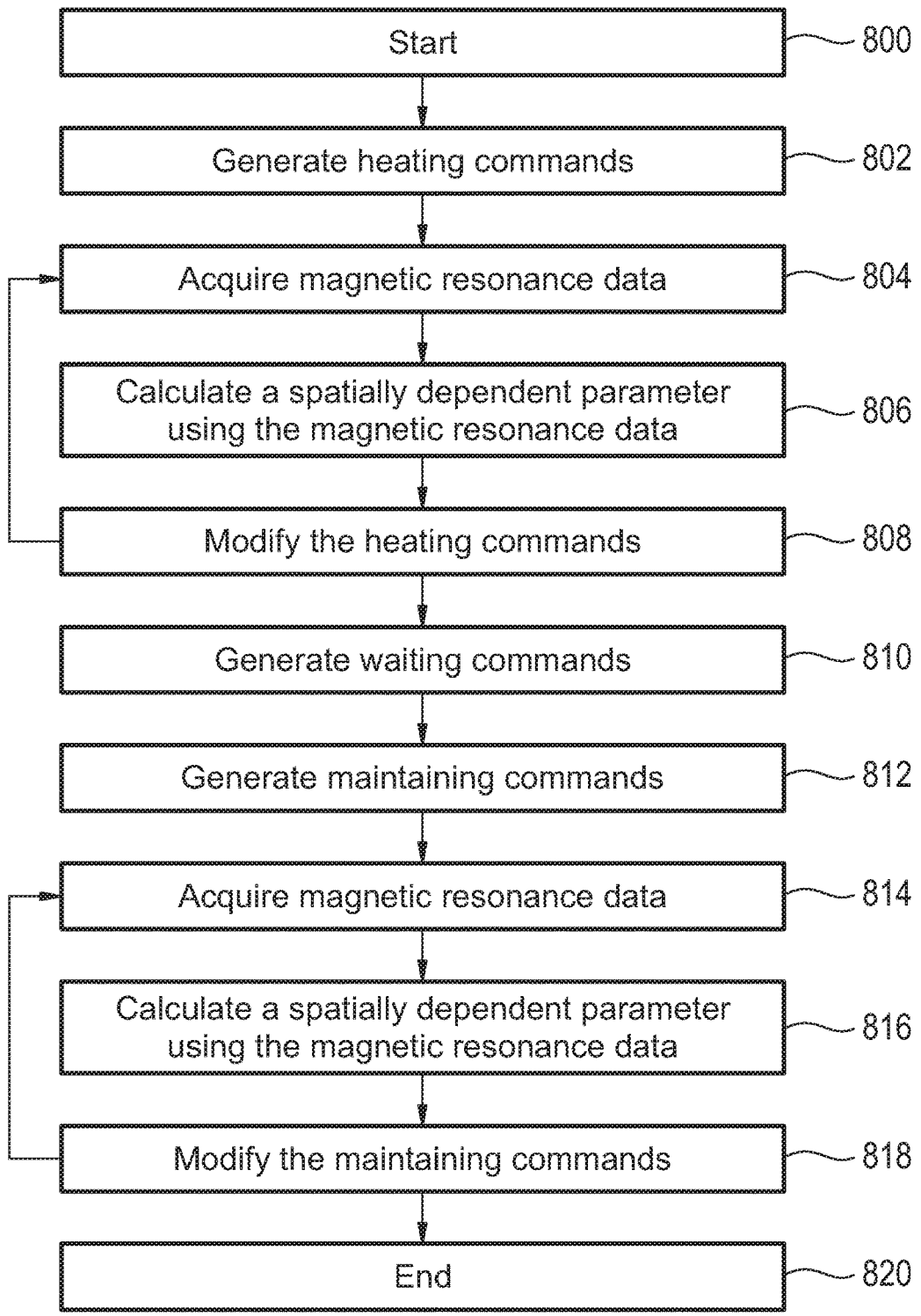
FIG. 8 shows a flow diagram which illustrates a method according to a further embodiment of the invention.

FIG. 8 shows another flow diagram which illustrates a further embodiment of the method according to the invention. Steps 702-708 of FIG. 7 correspond to steps 802-808 of FIG. 8. In step 800 the method starts. In step 802 heating commands are generated. In step 804 magnetic resonance data is acquired during sonication of the target zone. In step 806 a spatially dependent parameter is calculated using magnetic resonance data. In step 808 the heating commands are modified. As with FIG. 7 steps 804, 806 and 808 continue in a closed loop. After the target zone has been initially heated waiting commands are generated 810. After a predetermined period of time or when magnetic resonance thermometry detects a spatially dependent parameter has left its acceptable range maintaining commands are generated 812. The maintaining commands cause the sonication of the target zone to resume again. In step 814 more magnetic resonance data is acquired. In step 816 the spatially dependent parameter is calculated again using the magnetic resonance data. In step 818 the maintaining commands are modified. Steps 814, 816 and 818 form a closed loop. After the closed loop is performed in some embodiments the method may return after step 818 to the generated waiting command in step 810. When the method is completely finished it ends in step 820.

Figure 9:
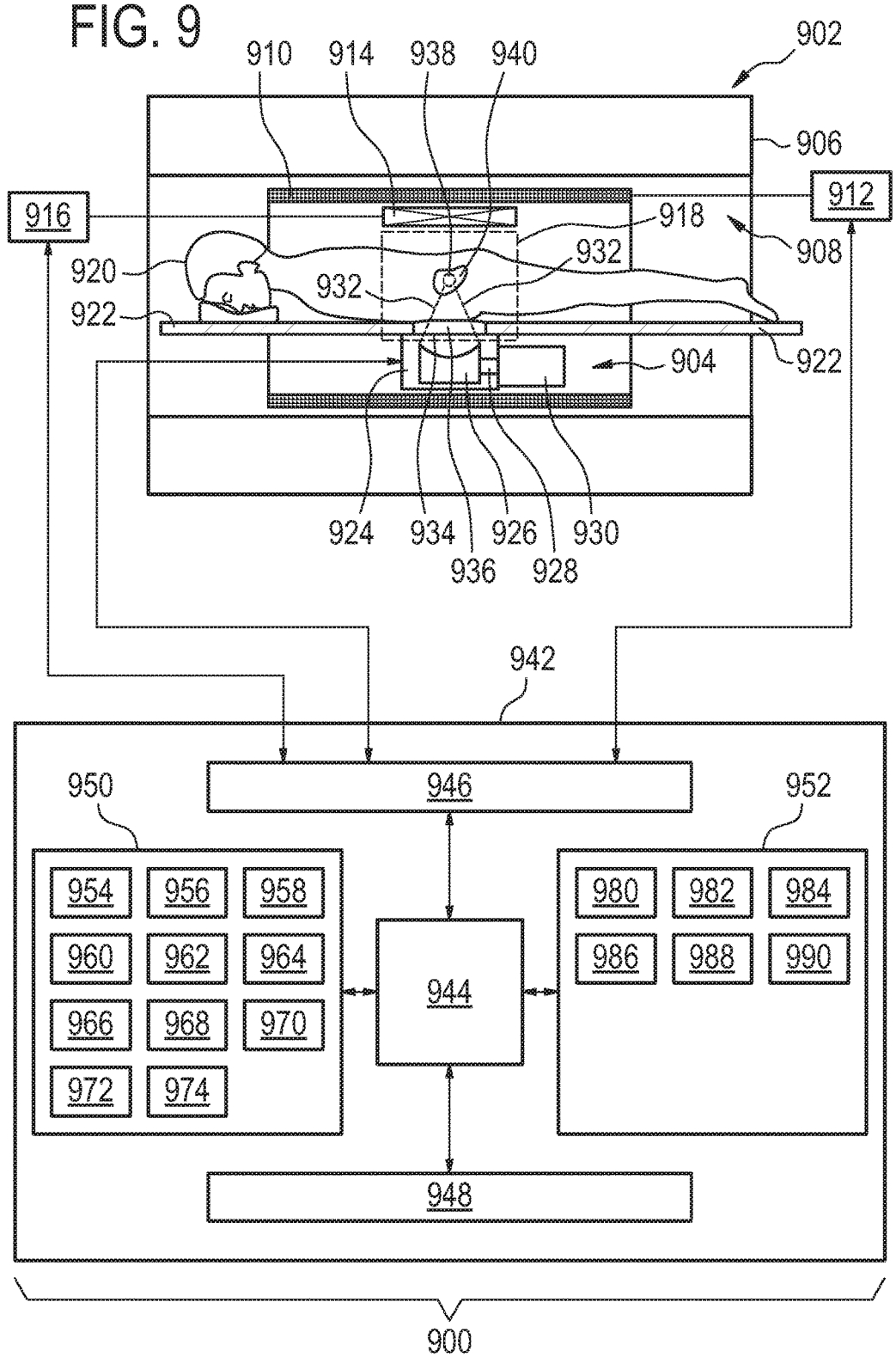
FIG. 9 shows a therapeutic apparatus according to an embodiment of the invention.

FIG. 9 shows a therapeutic apparatus 900 according to an embodiment of the invention. The therapeutic apparatus comprises a magnetic resonance imaging system 902 and a high-intensity focused ultrasound system 904. The magnetic resonance imaging system comprises a magnet 906. The magnet shown in FIG. 9 is a cylindrical type superconducting magnet. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 908 of the cylindrical magnet 906 there is an imaging zone where the magnetic field is strong and uniform enough to perform magnetic resonance imaging.

Within the bore 906 of the magnet there is also a magnetic field gradient coil 910 which is used to spatially encode magnetic spins within an imaging zone of the magnet during the acquisition of magnetic resonance data. The magnetic field gradient coil 910 is connected to a magnetic field gradient coil power supply 912. The magnetic field gradient coil is intended to be representative. Typically magnetic field gradient coils contain three separate sets of coils for spatially encoding in three orthogonal spatial directions. A magnetic field gradient power supply supplies current to the magnetic field gradient coils. The current supplied to the magnetic field coils is controlled as a function of time and may be ramped or pulsed.

In the center of the bore 908 is an imaging zone 918. Adjacent to the imaging zone is a radio-frequency coil 914 which is connected to transceiver 916. Also within the bore 908 is a subject 920 reposing on a subject support 922. The radio-frequency coil 914 is adapted for manipulating the orientations of magnetic spins within the imaging zone and for receiving radio transmissions from spins also within the imaging zone. The radio-frequency coil 914 may contain multiple coil elements. The radio-frequency coil may also be referred to as a channel or an antenna. The radio-frequency coil 914 and radio frequency transceiver 916 may be replaced by separate transmit and receive coils and a separate transmitter and receiver. It is understood that the radio-frequency coil 914 and the radio frequency transceiver 916 are representative. The radio-frequency coil 914 is intended to also represent a dedicated transmit antenna and a dedicated receive antenna. Likewise the transceiver may also represent a separate transmitter and receivers.

The high-intensity focused ultrasound system 904 comprises a fluid-filled chamber 924 which houses an ultrasound transducer 926. The ultrasound transducer 926 is mechanically positioned by a mechanical positioning system 928. There is an actuator 930 for actuating the mechanical positioning system. In alternative embodiments the ultrasound transducer may be a manually positioned external transducer without the fluid-filled chamber 924 or mechanical positioning system 928.

The ultrasonic transducer 926 may also contain multiple elements for emitting ultrasound. A power supply which is not shown may control the amplitude and/or phase and/or frequency of alternating current electric power supplied to the elements of the ultrasonic transducer 926. The dashed lines 932 show the path of ultrasound from the ultrasonic transducer 926. The ultrasound 932 first passes through the fluid-filled chamber 924. The ultrasound then passes through an ultrasound window 934. After passing through the ultrasound window 934 the ultrasound passes through an optional gel pad 936 which may be used to conduct ultrasound between the window 934 and the subject 920. The ultrasound 932 then enters the subject 920 and is focused into a focal or sonication point 938. There is a region 940 which is a target zone. Through a combination of electronic and mechanical positioning of the sonication point 938 the entire target zone 940 can be heated through a combination of heating and maintaining trajectories. The target zone 940 is within the imaging zone 918. The high-intensity focused ultrasound system 904, the transceiver 916, and the magnetic field gradient coil power supply 912 are all connected to a hardware interface 946 of computer system 942. The hardware interface 946 is connected to processor 944. The processor 944 is also connected to a user interface 948, computer storage 950, and computer memory 952.

The computer storage 950 is shown as containing magnetic resonance data 954 acquired with the magnetic resonance imaging system 902. The computer storage 950 further contains a magnetic resonance image 956 which is then reconstructed from the magnetic resonance data 954. In embodiments the magnetic resonance data 954 may also contain magnetic resonance thermometry data used for constructing a thermal map. Computer storage 950 is further shown as containing a treatment plan 958. The treatment plan 958 may contain data descriptive of the location of the target zone 940 relative to the anatomy of the subject 920. The computer storage is further shown as containing an image registration 960 to the magnetic resonance image 956. This for instance may be used for locating the target zone 940 in the magnetic resonance image 956. The computer memory 950 is further shown as containing a trajectory library 962. The trajectory library 962 may contain heating and/or maintaining trajectories. The computer storage 950 is further shown as containing heating commands 964, waiting commands 966 and maintaining commands 968. Computer storage 950 is further shown as containing a spatially dependent parameter 970. The spatially dependent parameter may be any one of the previously mentioned spatially dependent parameters. The computer storage 950 is also shown as containing a first predetermined threshold 972 and a second predetermined threshold 974.

The computer memory 952 contains computer executable code for operating the therapeutic apparatus 900. The computer memory 952 is shown as containing a control module 980 which contains computer executable code for controlling the operation and functioning of the therapeutic apparatus 900. The computer memory 952 is further shown as containing a command generation module 982 for generating the heating commands 964, the waiting commands 966, and the maintaining commands 968. The command generation module 982 is also adapted for modifying the heating commands 964, the waiting commands 966, and the maintaining commands 968. The computer memory 952 is further shown as containing a magnetic resonance control module 984. The magnetic resonance control module uses a pulse sequence 986 to control the operation and function of the magnetic resonance system 902. The pulse sequence 986 is also shown as being contained in the computer memory. The computer memory further contains an image reconstruction module 988 for reconstructing the magnetic resonance image 956 from the magnetic resonance data 954. The computer memory 952 is also shown as containing a trajectory generation module 990. The trajectory generation module 990 contains computer executable code for generating the heating and/or maintaining trajectories. The contents of the computer memory 952 may also be stored in the computer storage 950.

Figure 10:
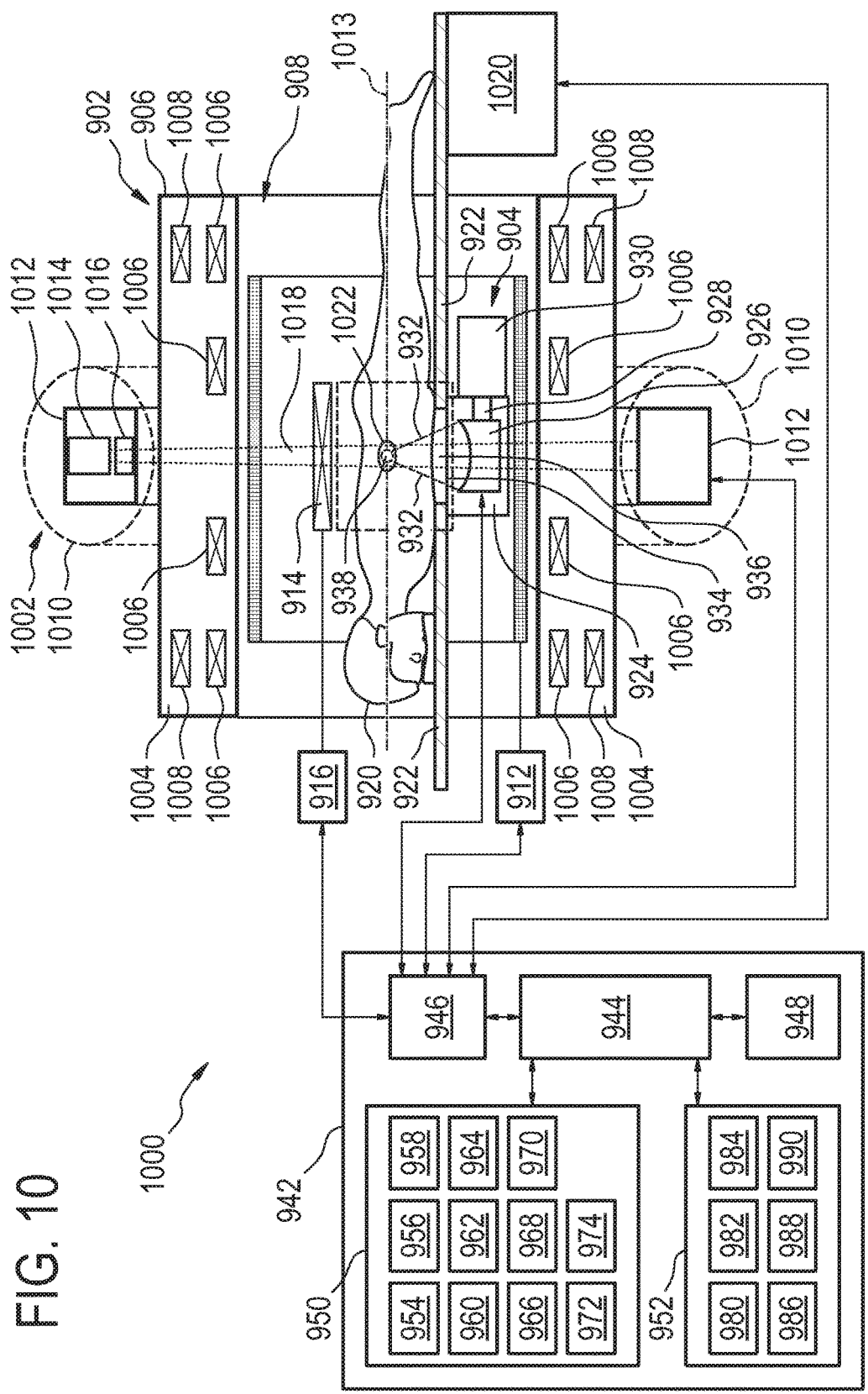
FIG. 10 shows a therapeutic apparatus according to a further embodiment of the invention.

FIG. 10 shows a further embodiment of a therapeutic system 1000 according to the invention. The embodiment shown in FIG. 10 is very similar to that shown in FIG. 9 and items labeled the same in both Figs. form equivalent functions. Items already discussed in FIG. 9 may not necessarily be the discussed in FIG. 10. The embodiment shown in FIG. 10 has had a radiation therapy system 1002 added to it. The magnet 906 is a superconducting magnet and more details are shown in this Fig. There is a cryostat 1004 with several superconducting coils 1006. There is also a compensation coil 1008 which creates an area of reduced magnetic field 1010 which surrounds the magnet 906. The radiation therapy system 1002 in this embodiment is intended to be representative of radiation therapy systems in general. The components shown here are typical for Linac and x-ray therapy systems. However with minor modifications such as using a split magnet charged particles or beta particle radiation therapy systems can also be illustrated using this diagram. There is a ring mechanism 1012 which is used to rotate a radiotherapy source 1014 about the magnet 906. The ring mechanism 1012 rotates about the axis of rotation 1013. There is a radiation therapy source 1014 which is rotated by the ring mechanism 1012. The radiotherapy source 1014 generates a radiation beam 1018 which passes through collimator 1016. In the Fig. the target zone is labeled 1022. In this example the target zone and the radiation target in the subject are identical. It can be noticed that the target zone 1022 is located on the axis of rotation 1013. As the radiation source 1014 rotates about the axis of rotation 1013 the target zone 1022 is always irradiated. There is also a support positioning system 1020 for positioning the support 922 to optimize the location of the target zone 1022 relative to the radiation therapy system 1014.

The radiation therapy system 1002 and the support positioning system 1020 are also connected to the hardware interface 946. The processor 944 through use of the control module 980 is able to control the operation and function of the entire therapeutic apparatus 1000.

FIGS. 11 to 14 show exemplary trajectories. These trajectories may either be heating trajectories and/or maintaining trajectories.

Figure 11:
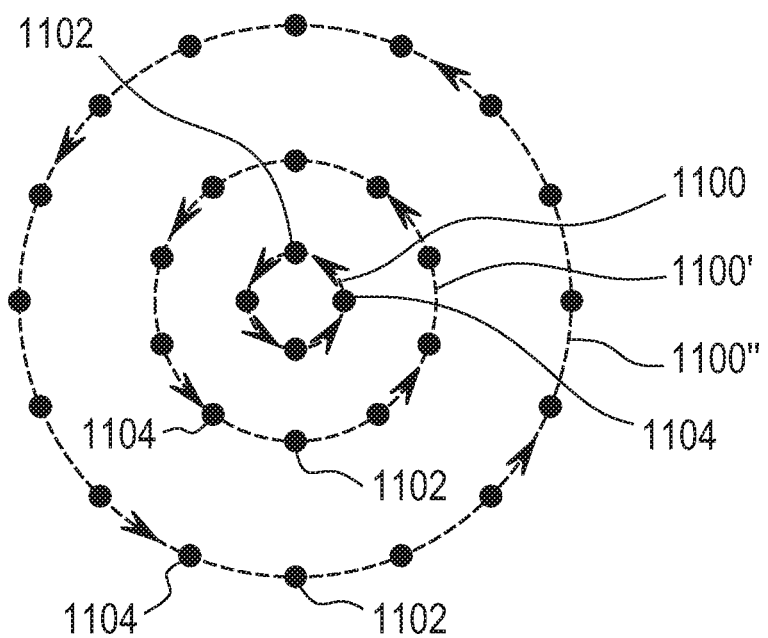
FIG. 11 illustrates a trajectory according to an embodiment of the invention.

In FIG. 11 there are three trajectories shown, 1100, 1100', and 1100". These trajectories 1100, 1100', 1100" are concentric circles. The dashed lines with arrows indicate the sequential order in which sonication points are performed. The large dots are the position of sonication points. Starting sonication points are labeled 1102 and ending sonication points are labeled 1104.

Figure 12:
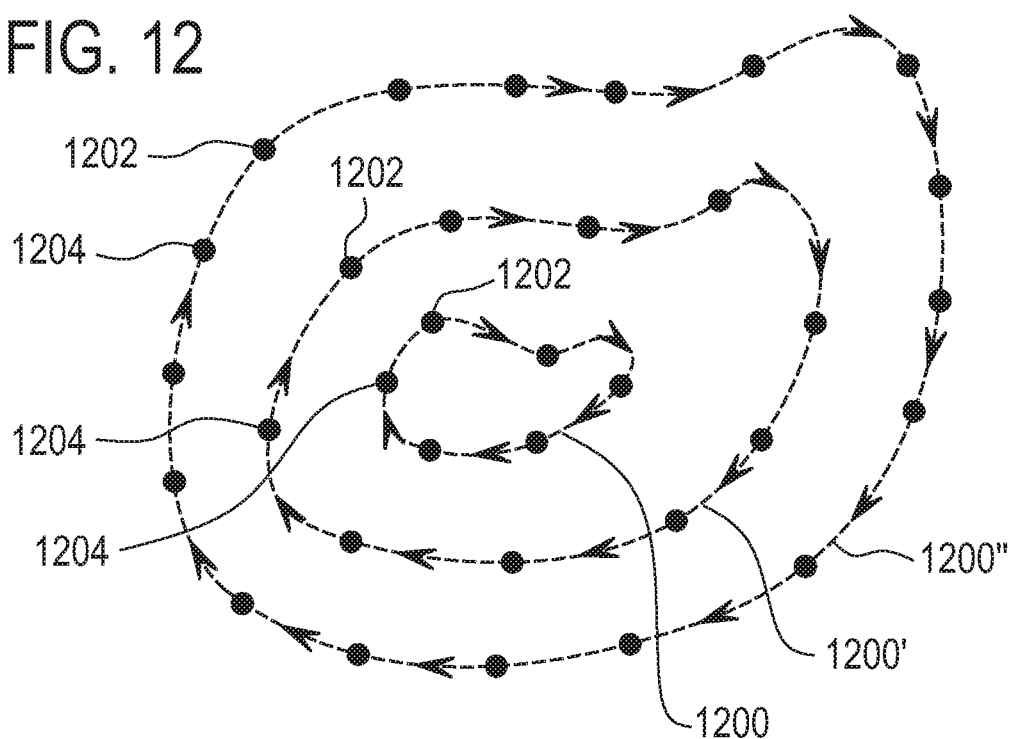
FIG. 12 illustrates a trajectory according to a further embodiment of the invention.

In FIG. 12 there are also three trajectories shown, 1200, 1200', 1200". The dashed lines again show the order in which sonications are performed. As with the last Fig. the dots indicate the location of sonication points. In this Fig. there are closed loops which are not circles for the trajectories 1200, 1200', 1200".

Figure 13:
FIG. 13 illustrates a trajectory according to a further embodiment of the invention.

In FIG. 13 a single sonication point 1300 is shown.

Figure 14:
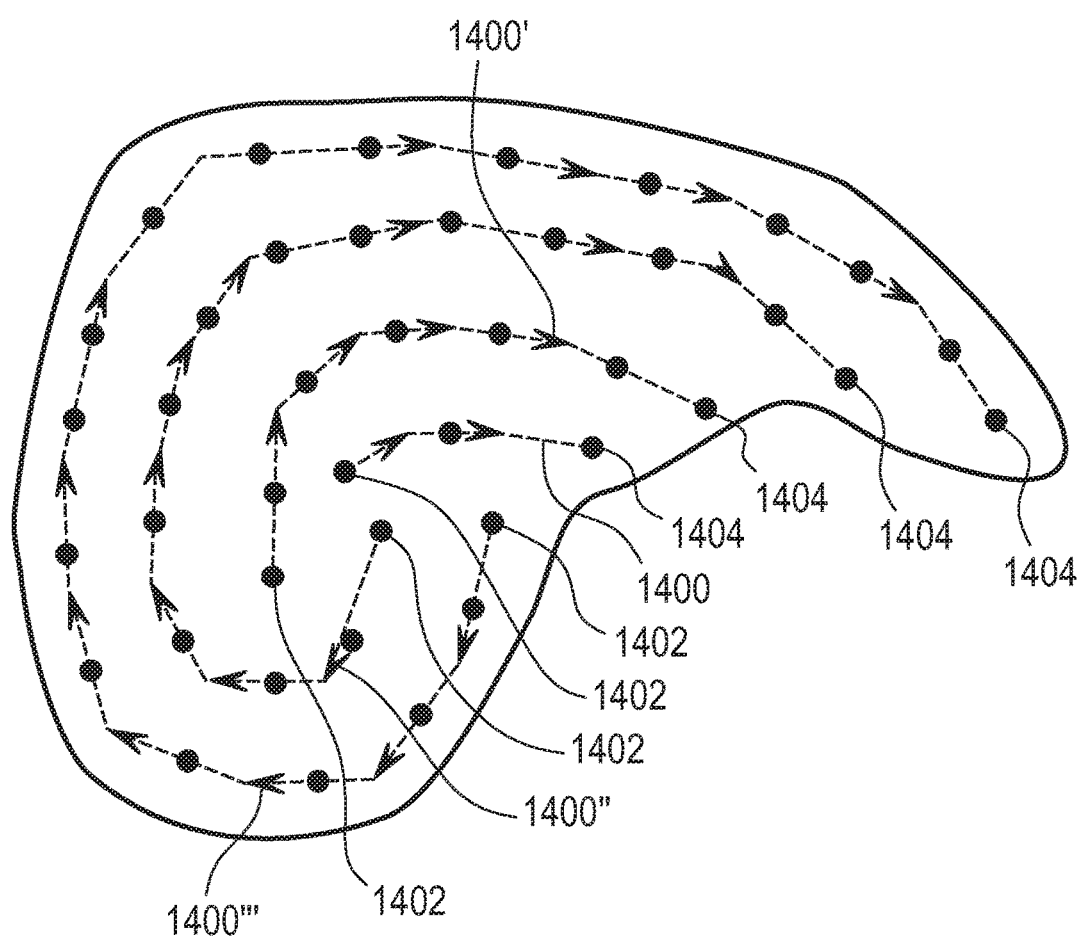
FIG. 14 illustrates a trajectory according to a further embodiment of the invention.

In FIG. 14 the trajectories are shown as linear patterns. There are five lines 1400, 1400', 1400", and 1400'''. These lines have arrows which show the order in which sonications are performed. Each trajectory 1400, 1400', 1400", and 1400''' has a starting sonication point 1402 and an ending sonication point 1404. As with FIGS. 11-13 the dots indicate the spatial location of a sonication. The trajectories 1400, 1400', 1400", 1400''' are arranged within an irregularly shaped target zone 1401. Depending upon the shape of the target zone 1401, it may be advantageous to use linear trajectories 1400, 1400', 1400", and 1400''' instead of circular loops or closed loops.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A therapeutic apparatus comprising:
a high intensity focused ultrasound system for heating a target zone of a subject;
a magnetic resonance imaging system for acquiring magnetic resonance data;
a processor for controlling the therapeutic apparatus;
a memory containing machine executable instructions for execution by the processor, wherein execution of the instructions cause the processor to generate heating commands which cause the high intensity focused ultrasound system to sonicate the subject in accordance with heating trajectories, the heating trajectories comprising a plurality of heating subtrajectories; wherein execution of the instructions further cause the processor to repeatedly:
acquire the magnetic resonance data during execution of the heating commands;
calculate a spatially dependent parameter from the magnetic resonance data;
modify the heating commands in accordance with the spatially dependent parameter such that within the target zone the spatially dependent parameter remains below a first predetermined threshold and above a second predetermined threshold; and
switch a sonication from a current heating subtrajectory to a subsequent heating subtrajectory based on switch criteria; and
wherein execution of the instructions further cause the processor to generate waiting commands which cause the high intensity focused ultrasound system to halt sonication for a predetermined period of time after executing the heating commands;
wherein execution of the instructions further cause the processor to generate maintaining commands which cause the high intensity focused ultrasound system to sonicate the subject in accordance with maintaining trajectories, the maintaining trajectories comprising a plurality of maintaining subtrajectories, wherein execution of the instructions further cause the processor to repeatedly:
acquire the magnetic resonance data during execution of the maintaining commands;
calculate the spatially dependent parameter from the magnetic resonance data acquired during execution of the maintaining commands; and
modify the maintaining commands in accordance with the spatially dependent parameter such that within the target zone the spatially dependent parameter remains below the first predetermined threshold and above the second predetermined threshold, wherein the maintaining commands cause the high intensity focused ultrasound system to sonicate a first maintaining subtrajectory when the spatially dependent parameter within the first maintaining subtrajectory falls below the first predetermined threshold during the predetermined time period.

2. The therapeutic apparatus of claim 1, wherein execution of the instructions further cause the processor to:
acquire repeatedly the magnetic resonance data during execution of the waiting commands;
trigger execution of the maintaining commands if the spatially dependent parameter in the target zone is below the second predetermined threshold.

3. The therapeutic apparatus of claim 1, wherein the spatially dependent parameter is any one of the following: proton signal intensity, maximum proton signal intensity, minimum proton signal intensity, mean proton signal intensity, median proton signal intensity, T1 signal intensity, maximum T1 signal intensity, minimum T1 signal intensity, mean T1 signal intensity, median T1 signal intensity, T2 signal intensity, maximum T2 signal intensity, minimum T2 signal intensity, mean T2 signal intensity, median T2 signal intensity, T2* signal intensity, minimum T2* signal intensity, maximum T2* signal intensity mean T2* signal intensity, mean T2* signal intensity, temperature, minimum temperature, mean temperature, median temperature, minimum ultrasonic dose, maximum ultrasonic dose, median ultrasonic dose, maximum temperature deviation, minimum signal intensity, maximum signal intensity, mean signal intensity, median signal intensity, minimum thermal dose, mean thermal dose, median thermal dose, and maximum thermal dose, and combinations thereof.

4. The therapeutic apparatus of claim 1, wherein the trajectories define any one of the following: concentric circles, concentric spheres, closed loops, closed surfaces, a single sonication location, and linear patterns.

5. The therapeutic apparatus of claim 1, wherein the instructions further cause the processor to:
receive medical image data;
receive a treatment plan, wherein the treatment plan is descriptive of the location of the target zone; and generate the heating trajectories in accordance with the medical image data and the treatment plan.

6. The therapeutic apparatus of claim 5, wherein execution of the instructions further causes the processor to:
receive magnetic resonance data from the magnetic resonance imaging system; and
reconstruct the medical image data from the magnetic resonance data.

7. The therapeutic apparatus of claim 1, wherein the therapeutic apparatus further comprises a radiation therapy system, wherein execution of the instructions further causes the processor to perform any one of the following: irradiate a radiation target in the subject after heating the target zone and irradiate the radiation target during heating of the target zone, and wherein the radiation target comprises at least a portion of the target zone.

8. The therapeutic apparatus of claim 7, wherein the radiation therapy system is any one of the following: a proton therapy system, an x-ray therapy system, a charged particle therapy system, a carbon ion therapy system, a gamma radiation source therapy system, beta particle therapy system, and a LINAC.

9. The therapeutic apparatus of claim 1, wherein execution of the instructions further cause the processor to:
repeatedly calculate a second spatially dependent parameter from the magnetic resonance data;
halt sonication of the target zone by the high intensity focused ultrasound system if a predetermined change in the second spatially dependent parameter occurs.

10. The therapeutic apparatus of claim 1, further comprising a thermometry module to measure temperature in a measurement field and in particular to compute a thermal dose, wherein execution of the instructions cause the processor to generate heating commands which cause the high intensity focused ultrasound system to sonicate the subject in accordance with heating trajectories on the basis of the measured temperature and/or thermal dose.

11. The therapeutic apparatus of claim 1, wherein the switch criteria comprise maximum time, minimum time, maximum temperature, minimum temperature, mean temperature, median temperature, minimum dose, maximum dose, median dose, maximum temperature deviation, minimum signal intensity, maximum signal intensity, mean signal intensity, or median signal intensity.

12. The therapeutic apparatus of claim 1, wherein execution of the instructions further causes the processor to:
determine that the spatially dependent parameter within the first maintaining subtrajectory and a second maintaining subtrajectory is below the first predetermined threshold during the predetermined time period;
determine a respective predetermined priority of the first and second maintaining subtrajectories; and
sonicate the first and second maintaining subtrajectories in an order according to their respective predetermined priority.

13. A non-transitory computer program product comprising machine executable instructions for execution by a processor controlling a therapeutic apparatus, wherein the therapeutic apparatus comprises a high intensity focused ultrasound system for heating a target zone of a subject, wherein the therapeutic apparatus further comprises a magnetic resonance imaging system for acquiring magnetic resonance data, wherein execution of the instructions causes the processor to generate heating commands, which cause the high intensity focused ultrasound system to sonicate the subject in accordance with heating trajectories, the heating trajectories comprising a plurality of heating subtrajectories, wherein execution of the instructions further cause the processor to repeatedly:
acquire the magnetic resonance data during execution of the heating commands;
calculate a spatially dependent parameter from the magnetic resonance data;
modify the heating commands in accordance with the spatially dependent parameter such that within the target zone the spatially dependent parameter remains below a first predetermined threshold and above a second predetermined threshold; and
switch a sonication from a current heating subtrajectory to a subsequent heating subtrajectory based on switch criteria;
wherein execution of the instructions further cause the processor to generate waiting commands which cause the high intensity focused ultrasound system to halt sonication for a predetermined period of time after executing the heating commands;
wherein execution of the instructions further cause the processor to generate maintaining commands which cause the high intensity focused ultrasound system to sonicate the subject in accordance with maintaining trajectories, the maintaining trajectories comprising a plurality of maintaining subtrajectories, wherein execution of the instructions further cause the processor to repeatedly:
acquire the magnetic resonance data during execution of the maintaining commands;
calculate the spatially dependent parameter from the magnetic resonance data acquired during execution of the maintaining commands; and
modify the maintaining commands in accordance with the spatially dependent parameter such that within the target zone the spatially dependent parameter remains below the first predetermined threshold and above the second predetermined threshold, wherein the maintaining commands cause the high intensity focused ultrasound system to sonicate a first maintaining subtrajectory when the spatially dependent parameter within the first maintaining subtrajectory falls below the first predetermined threshold during the predetermined time period.

14. The non-transitory computer program product of claim 13, wherein the switch criteria comprise maximum time, minimum time, maximum temperature, minimum temperature, mean temperature, median temperature, minimum dose, maximum dose, median dose, maximum temperature deviation, minimum signal intensity, maximum signal intensity, mean signal intensity, or median signal intensity.

15. The non-transitory computer program product of claim 13, wherein execution of the instructions further causes the processor to:
determine that the spatially dependent parameter within the first maintaining subtrajectory and a second maintaining subtrajectory is below the first predetermined threshold during the predetermined time period;
determine a respective predetermined priority of the first and second maintaining subtrajectories; and
sonicate the first and second maintaining subtrajectories in an order according to their respective predetermined priority.

16. A method of operating a therapeutic apparatus, wherein the therapeutic apparatus comprises a high intensity focused ultrasound system for heating a target zone of a subject, wherein the therapeutic apparatus further comprises a magnetic resonance imaging system for acquiring magnetic resonance data, wherein the method comprises the steps of generating heating commands which cause the high intensity focused ultrasound system to sonicate the subject in accordance with heating trajectories, the heating trajectories comprising a plurality of heating subtrajectories, wherein the method comprises the steps of repeatedly:

acquiring the magnetic resonance data during execution of the heating commands;

calculating a spatially dependent parameter from the magnetic resonance data; and modifying the heating commands in accordance with the spatially dependent parameter such that within the target zone the spatially dependent parameter remains below a first predetermined threshold and above a second predetermined threshold;

switching a sonication from a current heating subtrajectory to a subsequent heating subtrajectory based on switch criteria;

generating waiting commands which cause the high intensity focused ultrasound system to halt sonication for a predetermined period of time after executing the heating commands; further to generate maintaining commands which cause the high intensity focused ultrasound system to sonicate the subject in accordance with maintaining trajectories, the maintaining trajectories comprising a plurality of maintaining subtrajectories, and to repeatedly:

acquiring the magnetic resonance data during execution of the maintaining commands;

calculating the spatially dependent parameter from the magnetic resonance data acquired during execution of the maintaining commands; and modifying the maintaining commands in accordance with the spatially dependent parameter such that within the target zone the spatially dependent parameter remains below the first predetermined threshold and above the second predetermined threshold, wherein the maintaining commands cause the high intensity focused ultrasound system to sonicate a first maintaining subtrajectory when the spatially dependent parameter within the first maintaining subtrajectory falls below the first predetermined threshold during the predetermined time period.

17. The method of claim 16, wherein the switch criteria comprise maximum time, minimum time, maximum temperature, minimum temperature, mean temperature, median temperature, minimum dose, maximum dose, median dose, maximum temperature deviation, minimum signal intensity, maximum signal intensity, mean signal intensity, or median signal intensity.

18. The method of claim 16, further comprising:

determining that the spatially dependent parameter within the first maintaining subtrajectory and a second maintaining subtrajectory is below the first predetermined threshold during the predetermined time period;

determining a respective predetermined priority of the first and second subtrajectories; and sonicating the first and second maintaining subtrajectories in an order according to their respective predetermined priority.

* * * * *